US00PP10859P

United States Patent [19]

Wain

[11] Patent Number: Plant 10,859

[45] Date of Patent: Apr. 13, 1999

[54] CHRYSANTHEMUM PLANT NAMED 'PEACE TIME'

[75] Inventor: Peter Wain, Portsmouth, United Kingdom

[73] Assignee: Cleangro, Ltd., West Sussex, United Kingdom

[21] Appl. No.: 08/838,356

[22] Filed: Apr. 8, 1997

[51] Int. Cl.[6] ..... A01H 5/00

[52] U.S. Cl. ..... Plt./288

[58] Field of Search ..... Plt./77, 288

*Primary Examiner*—Howard J. Locker

*Attorney, Agent, or Firm*—Christie, Parker & Hale, LLP

[57] ABSTRACT

A new plant variety of Chrysanthemum having white flowers with yellow/cream and green centers.

2 Drawing Sheets

BACKGROUND OF THE INVENTION

The present invention is directed to a new and distinct variety of Chrysanthemum botanically classified as *Dendranthema grandiflora*. The varietal denomination of the new chrysanthemum is 'Peace Time.'

The female and male parents of the new variety are undistributed, unpatented seedlings identified as P132-18 and P12-2, respectively. The new variety has been asexually reproduced by vegetative cuttings in Ventura County, Calif. and the distinguishing characteristics are retained through successive generations of asexual reproduction.

SUMMARY OF THE INVENTION

'Peace Time' is a spray type pot forcing Chrysanthemum plant variety producing white with green and cream (yellow) centers and capable of being grown commercially in a greenhouse.

BRIEF DESCRIPTION OF ILLUSTRATIONS

The accompanying photographs show typical specimens of the new variety with colors being as nearly true as possible with illustrations of this type. One illustration shows 'Peace Time' grown as a pinched pot mum and the other illustration is a close-up of the flowers.

DESCRIPTION OF THE PLANT

The following description of the new variety is of specimens grown in a greenhouse in Oxnard, Ventura County, Calif. in the month of October. 'Peace Time' has not been observed under all possible environmental conditions. The phenotype may vary significantly with variations in the environment such as temperature, light intensity, day length and cultural conditions. Color values provided in the description are from The Royal Horticultural Society Colour Charts (RHSCC), unless otherwise indicated.

Plants of the new variety have been grown successfully under temperature conditions averaging about 65° F. at night and about 75° to 85° F. during the day under light conditions of about 5,000–6,000 foot candles. The plants respond well to use of growth retardant, such as a one B-9 treatment at about 2000 ppm. To produce a commercial product the plants may be pinched twice. It has been observed that the shelf life (typical lastingness of a single bloom on the plant) of 'Peace Time' is about 21 days with the response time of about 9.5 weeks.

Plant

Habit: About ½ upright.

Height: About 24.5 cm, after application of growth retardant as described.

Branching characeristics: Prolific brancher.

Typical container size to be grown in: 4", 6", 8", 10".

Length of lateral branches: Averge — about 11 cm.

Stem Color: Near 138B.

Foliage

Leaf arrangement: Alternate.

Number of leaves per lateral branch: Average — about 10.

(1) *Size. Length — Average about* 9.8 cm. Width — Average about 5.5 cm.

(2) *Shape.*—Ovate.

(3) *Attachment.*—Petioled.

(4) *Apex.*—Acute with serrate tip.

(5) *Base.*—Tapered.

(6) *Color.*—Mature, Young

Top.—Near 137C, Near 137A

Bottom.—Near 146B, Near 137C

Margin: Deeply, lobed with serrations.

Aspect: Mostly flat, cupped under slightly.

Surface characteristics: Top-puberulent. Bottom-puberulent.

Venation: Palmately net, main veins prominent on underside of leaf and coloration is near 146D, veinlet coloration is near 146B.

Petiole:

(1) *Length.*—About 2.6 cm.

(2) *Color.*—Near 146D.

(3) *Other characteristics.*—Winged.

Stipule: Infrequently, 1 or 2 on a mature leaf; 1 or 2 deep lobes, acute tipe, under about 0.4 cm.

Flower

Inflorescence form: Cymose cluster.

Flower form: Decorative.

Flower shape: Flat capitulum.

Flower color (general): White with yellow/cream and green, coloration of center of bloom is near 154D, about 2 cm diameter: As flowers age, the center becomes more obvious and changes to near 154A.

Blooms: About 2 to 3 blooms per branch.

(1) *Diameter.*—About 8 cm.

(2) *Depth.*—About 2 cm.

Sepal:

(1) *Number.*—About 200, the sepals are not arranged in regular whorls but are found mixed throughout the ray florets; there are a large number of tightly held ray florets in the center of the bloom which combined with the sepals creates the appearance of a green-yellow eye on each bloom.

(2) *Color.*—Near 148B.

(3) *General appearance.*—Slight membranous margin, acute tip, flat.

Peduncle:

(1) *Length.*—Average about 5 cm.

(2) *Habit.*—Completely straight.

(3) *Surface.*—Tomentose.

(4) *Color.*—Near 148B.

(5) *Strength.*—Very strong.

Bud:

(1) *Shape.*—Flattened sphere.

(2) *Diameter.*—Avg. about 0.8 cm.

(3) *Color.*—Near 148A.

(4) *Height.*—About 0.4 cm.

Ray florets:

(1) *Number per flower.*—About 420; ray florets are channeled, 8 to 12 channels per ray floret.

(2) *Fused.*—No.

(3) *Texture.*—Matte, many deep ridges. p2 (4) *Shape.*—Elliptic.

(5) *Apex.*—Many lobes, variable number and depth, overall shape is flat.

(6) *Base.*—Tapered, fused just before base.

(7) *Margin.*—Entire.

(8) *Aspect.*—Curled under, some reflex back, many flat.

(9) *Length.*—Avg. about 4.1 cm.

(10) *Width.*—Avg. about 1.3 cm.

*Color — top side.*—Immature: Near 155B. Mature: Near 155B. Fading: Near 155D.

*Color — under side.*—Immature: Near 155B. Mature: Near 155D. Fading: Near 155D.

Disc florets:

(1) *Number per flower.*—About 70.

(2) *Texture.*—Shiny.

(3) *Shape.*—Cylindric.

(4) *Margin.*—Entire.

(5) *Length.*—About 0.4 cm.

(6) *Width.*—About 0.1 cm.

(7) *Fragrance.*—Very faint.

*Color.*—Immature: Near 12C. Mature: Near 26B with pale green tip. Fading: Near 22A.

Description of flower as it ages: Tips brown, large green center is exposed, flower stays flat.

Reproductive Organs

Ray florets: Pistillate.

Pistillate:

(1) *Pistil number.*—1 per flower.

(2) *Ovary shape.*—Bulbous sphere with domed top.

(3) *Stigma shape.*—Linear, flared outward.

(4) *Stigma color.*—Near 9A.

(5) *Style length.*—About 0.4 cm.

(6) *Style color.*—Translucent.

Disc florets:

*Pistillate.*—(1) Pistil number: 1 per flower. (2) Stigma shape: Linear. (3) Style length: About 0.2 cm, translucent.

*Staminate.*—(1) Stamen number: 5. (2) Anther length: About 0.2 cm. (3) Anther shape: Linear, near 167C. (4) Pollen quantity: Not present.

What is claimed is:

1. A new and distinct variety of Chrysanthemum plant substantially as herein shown and described.

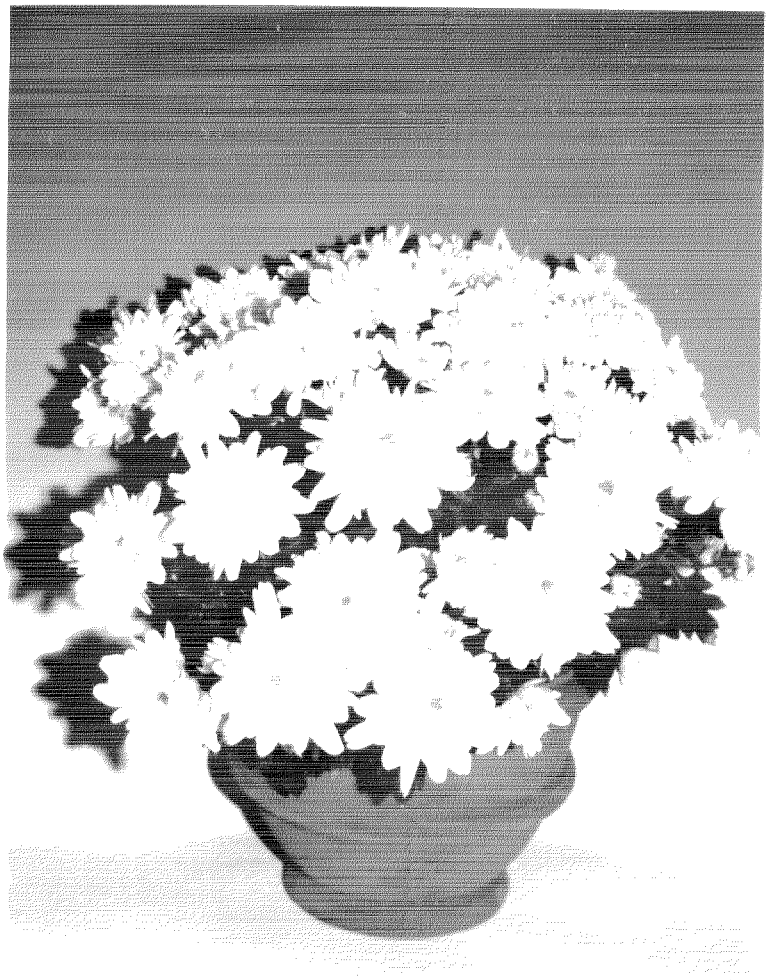

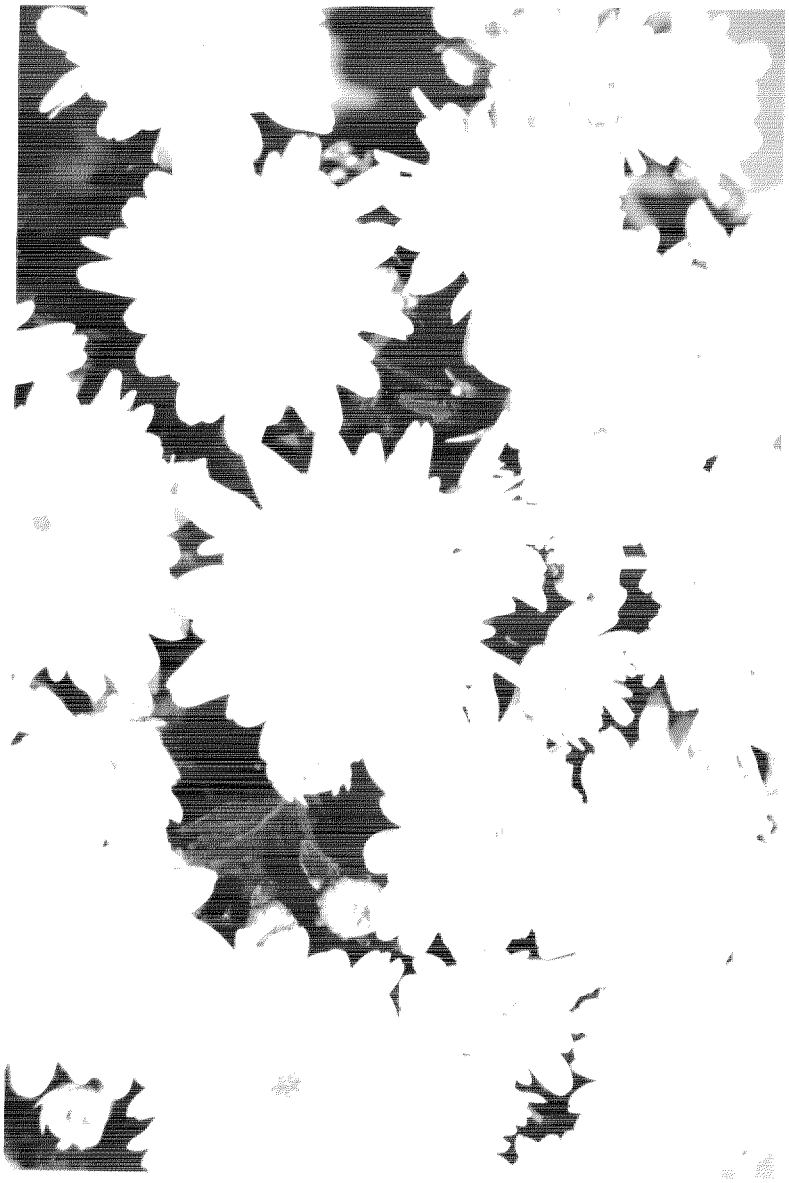

* * * * *